(12) United States Patent
Nogueira et al.

(10) Patent No.: US 12,290,580 B1
(45) Date of Patent: May 6, 2025

(54) SHOWER GEL CHASSIS FORMULATION

(71) Applicant: Kenvue Brands LLC, Summit, NJ (US)

(72) Inventors: Ana Carolina Nogueira, Skillman, NJ (US); Euen Ekman-Gunn, Skillman, NJ (US)

(73) Assignee: Kenvue Brands LLC, Summit, NJ (US)

( * ) Notice: Subject to any disclaimer, the term of this patent is extended or adjusted under 35 U.S.C. 154(b) by 357 days.

(21) Appl. No.: 17/848,486

(22) Filed: Jun. 24, 2022

Related U.S. Application Data

(60) Provisional application No. 63/216,894, filed on Jun. 30, 2021.

(51) Int. Cl.
| | | |
|---|---|---|
| *A61K 8/00* | (2006.01) |
| *A61K 8/04* | (2006.01) |
| *A61K 8/34* | (2006.01) |
| *A61K 8/368* | (2006.01) |
| *A61K 8/44* | (2006.01) |
| *A61K 8/60* | (2006.01) |
| *A61K 8/73* | (2006.01) |
| *A61K 8/9717* | (2017.01) |
| *A61K 8/9794* | (2017.01) |
| *A61Q 19/10* | (2006.01) |

(52) U.S. Cl.
CPC ............... *A61K 8/04* (2013.01); *A61K 8/345* (2013.01); *A61K 8/368* (2013.01); *A61K 8/44* (2013.01); *A61K 8/602* (2013.01); *A61K 8/73* (2013.01); *A61K 8/9717* (2017.08); *A61K 8/9794* (2017.08); *A61Q 19/10* (2013.01)

(58) Field of Classification Search
None
See application file for complete search history.

(56) References Cited

U.S. PATENT DOCUMENTS

| | | | | |
|---|---|---|---|---|
| 2011/0150812 A1* | 6/2011 | Mecca | ..................... | A61Q 5/12 |
| | | | | 424/70.19 |
| 2022/0202670 A1* | 6/2022 | Koshti | ..................... | A61K 8/35 |

OTHER PUBLICATIONS

Cosme Bio Labeling; 2022—https://www.cosmebio.org/en/cosmebio-label/.

* cited by examiner

*Primary Examiner* — Necholus Ogden, Jr.
(74) *Attorney, Agent, or Firm* — Samuel J. Gee

(57) ABSTRACT

A shower cream chassis composition and its preparation method are disclosed.

7 Claims, No Drawings

SHOWER GEL CHASSIS FORMULATION

CROSS-RELATED APPLICATION

The present application claims the benefit of the earlier filing date of U.S. patent application 63/216,894, filed Jun. 30, 2021, the entirety of which application is hereby incorporated by reference herein as if fully set forth herein.

FIELD

The invention relates to the field of cosmetics, in particular to a shower cream chassis composition and its preparation method.

BACKGROUND

Bath products, especially shower creams, have become indispensable daily necessities in modern life. With the increasing awareness of health, more and more consumers now prefer natural green products. However, most of the shower creams on the market today are made of chemical substances, and their functions are mostly limited to washing. Most bath products use sulfates as the main surfactant to strengthen the cleaning and decontamination ability of the product. However, although these substances have strong surface degreasing power, they can be irritating to sensitive skin.

A shower cream with mild performance, good washing properties, and ability to soften of the skin is desired.

SUMMARY

In an aspect, the invention is a shower cream chassis composition comprised of naturally derived ingredients that moisturizes and softens dry, damaged skin that provides immediate and long lasting results.

A single shower cream chassis composition can be used to prepare a number of different final shower cream compositions to enable personalization.

The shower cream chassis composition contains extra-gentle, organic and silicon-free ingredients.

The shower cream chassis composition is a unique composition that can be used both as a rinse-off or a leave-in product.

The shower cream chassis composition meets consumer expectations, in terms of aesthetics while bringing flexibility, simplicity and innovation to the products.

Ideally, the shower cream chassis composition and the final shower cream compositions qualify for Cosmébio labeling (https://www.cosmebio.org/en/cosmebio-label/). In order to use a Cosmébio label on a product's packaging, a natural or organic cosmetic must follow certain conditions in regard to the composition of its ingredients. One requirement is that 95% to 100% of the ingredients of the total product must be of natural origin (with water and mineral or mineral-based ingredients considered as natural).

The aesthetics (appearance and consistency) of the shower cream chassis composition of the invention meets or exceeds commercially available benchmark shower cream products.

The shower cream chassis composition of the invention is cost effective.

The final shower cream compositions may contain additional ingredients, including but not limited to, fragrance.

The shower cream chassis of the present invention is preferably used in personal cleansing applications nonexclusively including shampoos, creams such as shower creams (otherwise known as shower gels), baths such as baby baths, washes such as body washes, and the like.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

DETAILED DESCRIPTION OF THE EMBODIMENTS

The invention relates to a shower cream chassis composition and its method of preparation.

The shower cream chassis composition may be prepared using the following raw materials:
  Sodium Benzoate;
  Sodium Cocoyl Glutamate;
  Glycerin (vegetable origin);
  Coco-Glucoside;
  Xanthan gum;
  Carrageenan;
  Aloe vera; and
  Caprylyl/Capryl Glucoside;
  wherein 95% to 100% of the ingredients of the total product are of natural origin.

The shower cream chassis composition may be manufactured batchwise or using a continuous process. The continuous process is particularly preferred, especially, when heating of at least one component and cooling is required after mixing. The subject matter according to the invention thus includes a continuous process for manufacturing a shower cream chassis composition, in which a preparation that is heated, mixed, and cooled in a continuous fashion.

The shower cream chassis composition, which is ecologically and environmentally friendly, nourishes and moistens the skin.

The shower cream chassis composition meets consumer expectations for those different applications, in terms of aesthetics while bringing flexibility, simplicity and innovation to the products.

Ideally, the shower cream chassis composition and the shower cream compositions qualify for Cosmébio labeling (https://www.cosmebio.org/en/cosmebio-label/). In order to use a Cosmébio label on a product's packaging, a natural or organic cosmetic must follow certain conditions in regard to the composition of its ingredients. One requirement is that 95% to 100% of the ingredients of the total product must be of natural origin (with water and mineral or mineral-based ingredients considered as natural).

The shower cream chassis composition of the invention meets the following requirements.
  1-week stability at 60° C., appearance must be compatible with sample at room temperature (RT), no separation is accepted;
  Viscosity values fresh, 24 hours (h) and 1 week at RT at pH 4.5 (minimal of the range) and at pH 6.0 (max)- (target range: . . . cPs, RVT spindle 6, 25° C.). Available benchmark shower cream product is used as reference for viscosity at 1 week;
  Foaming (similar to commercially available benchmark);
  Clarity (similar to commercially available benchmark);
  Rheology/Flow (similar to commercially available benchmark);

pH values fresh, 24 h and 1-week at RT. pH range is 4.2-4.8;

Skin feel (measured by sensorial perception or skin moisturization);

The shower cream chassis composition of the invention preferably contains the following ingredients:

Sodium Benzoate at 1.0% as preservative;
Sodium Cocoyl Glutamate—up to 1.4%;
Glycerin (vegetable origin)—up to 2%;
Coco-Glucoside—up to 4%;
Xanthan gum—up to 0.45%;
Carrageenan—up to 0.25%;
Aloe vera—up to 0.06%; and
Caprylyl/Capryl Glucoside—up to 1.25%.

The shower cream chassis composition meets the full stability requirements below, which is done in the in standard stability glass jar without addition of fragrance or concept ingredients.

3 months at 5° C.±3° C.: used as Control for comparison of appearance (physical conditions, for example, color, odor, appearance);

3 months at 25° C.±2° C./60%±5% RH (measurements of pH and viscosity, initial and 3 months);

3 months and 6 months at 40° C.±2° C./75%±5% RH (measurements of pH and viscosity at 1, 3 and 6 months); and 1 month at 50° C. (measurements of pH and viscosity at 1 month).

F/T: Perform 3 cycles. Full physical testing after the third cycle. Each cycle will be 24 to 48 hours at −10° C. to −20° C. and 24 to 48 hours at 40° C.

The shower cream chassis composition meets micro testing requirements.

The shower cream chassis composition meets the in-vivo and in-vitro tests described below.

In-vivo test: Sensorial panel test with minimum 30 panelists of different skin type. Panelists are evaluated using a detailed questionnaire.

In-vitro tests: Commercially available benchmark shower cream product is used as comparison in all tests below. The shower cream chassis composition and/or shower cream final composition is evaluated as both rinse-off and leave-in product.

Skin moisturization
  Deliverable: trans epithelial water loss (TEWL) results up to 24 h The shower cream chassis composition and/or shower cream final composition meet the following compliance requirements:

Qualify for Cosmebio labeling/Ecocert certification;
All raw materials in the compositions comply with the chemical restrictions of regulatory bodies and influential retailers;
Banned or non-compliant preservatives, including but not limited to formaldehyde, methylisothiazolinone, methylchloroisothiazolinone, quaternium-15, and parabens, are not present in raw materials or added to the compositions;
Sulfate-free surfactant system for any cleansers;
Does not contain State of California Proposition 65 ingredients, including, but not limited to, cocamide DEA, MIPA, MEA, or TEA (including residual solvents and impurities of raw materials);
Does not contain palm oil/palm kernel oil.

Success Criteria

The shower cream chassis composition and shower cream final composition deliver on must-have attributes including that they permit continuous manufacturing process with performance similar to benchmark.

In all embodiments of the present composition, all percentages are by weight of the total composition, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity.

All percentages are calculated by weight unless otherwise indicated. All percentages are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention claimed is:

1. A shower cream chassis composition comprising:
Sodium Benzoate;
Sodium Cocoyl Glutamate;
Glycerin;
Coco-Glucoside;
Xanthan gum;
Carrageenan;
Aloe vera;
Caprylyl/Capryl Glucoside;
wherein 95% to 100% by weight of the ingredients of the shower cream chassis composition are of natural origin.

2. A process for manufacturing the shower cream chassis composition of claim 1, comprising:
mixing one or more of the ingredients recited in claim 1 at a temperature greater than about 25° C. to about 40° C.; and
continuing to mix the one or more ingredients while allowing the one or more ingredients to cool to a temperature of about 25° C. to about 40° C.

3. The shower cream chassis composition of claim 1, wherein:
the sodium benzoate is provided at less than 5.0% by weight;
the sodium cocoyl glutamate is provided at less than or equal to 5.0% by weight;
the glycerin is provided at less than or equal to 5.0% by weight;
the coco-glucoside is provided at less than or equal to 5.0% by weight;
the xanthan gum is provided at less than or equal to 1.0% by weight;
the carrageenan is provided at less than or equal to 1.0% by weight;
the aloe vera is provided at less than or equal to 1.0% by weight; and
the caprylyl/capryl glucoside is provided at less than or equal to 2.0% by weight.

4. The shower cream chassis composition of claim 1, wherein:
- the sodium benzoate is provided at 1.0% by weight;
- the sodium cocoyl glutamate is provided at less than or equal to 1.4% by weight;
- the glycerin is provided at less than or equal to 2.0% by weight;
- the coco-glucoside is provided at less than or equal to 4.4% by weight;
- the xanthan gum is provided at less than or equal to 0.45% by weight;
- the carrageenan is provided at less than or equal to 0.25% by weight;
- the aloe vera is provided at less than or equal to 0.06% by weight; and
- the caprylyl/capryl glucoside is provided at less than or equal to 1.25% by weight.

5. The shower cream chassis composition of claim 1, wherein the shower cream chassis composition is free of sulfates.

6. The shower cream chassis composition of claim 1, wherein the shower cream chassis composition is free of palm oil and palm kernel oil.

7. The shower cream chassis composition of claim 1, wherein the shower cream chassis composition is free of formaldehyde, methylisothiazolinone, methylchloroisothiazolinone, quaternium-15, and parabens.

* * * * *